United States Patent [19]

Scholes

[11] Patent Number: 4,489,005
[45] Date of Patent: Dec. 18, 1984

[54] PROCESS FOR THE PREPARATION OF CYCLOPROPANE COMPOUNDS

[75] Inventor: Gary Scholes, Amsterdam, Netherlands

[73] Assignee: Shell Oil Company, Houston, Tex.

[21] Appl. No.: 532,413

[22] Filed: Sep. 15, 1983

[30] Foreign Application Priority Data

Sep. 22, 1982 [GB] United Kingdom ............. 8227086

[51] Int. Cl.$^3$ ................ C07F 1/10; C07C 121/46
[52] U.S. Cl. .................... 260/430; 260/464
[58] Field of Search ................... 260/464, 430

[56] References Cited

U.S. PATENT DOCUMENTS

| | | | |
|---|---|---|---|
| 4,154,952 | 3/1979 | Schultz | 260/464 X |
| 4,195,033 | 3/1980 | Punja | 260/464 |
| 4,198,347 | 4/1980 | Punja | 260/464 |
| 4,205,009 | 5/1980 | Onore et al. | 260/464 |
| 4,243,677 | 1/1981 | Engel | 260/464 X |
| 4,250,326 | 2/1981 | Fishman | 260/464 X |
| 4,284,582 | 8/1981 | Kaye et al. | 260/464 |
| 4,305,885 | 12/1981 | Hanack et al. | 260/464 |
| 4,307,033 | 12/1981 | Hoffmann et al. | 260/464 |
| 4,332,745 | 6/1982 | Maurer et al. | 260/464 |

FOREIGN PATENT DOCUMENTS

| | | |
|---|---|---|
| 855691 | 12/1977 | Belgium . |
| 3683 | 8/1979 | European Pat. Off. . |
| 64781 | 4/1981 | European Pat. Off. . |
| 1520023 | 8/1978 | United Kingdom . |

OTHER PUBLICATIONS

Bahurel et al., *Bull. de La Soc. Chem. de France*, (1971) pp. 2209–2222.
*CA* 75: 88161K, Bahurel et al., (1971).

Primary Examiner—Joseph Paul Brust

[57] ABSTRACT

Compounds of the general formula

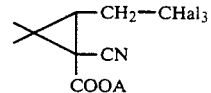

in which a chlorine or bromine atom and A represents a hydrogen or metal atom or an alkyl group of 1 to 4 carbon atoms, are prepared by cyclizing a compound of the general formula

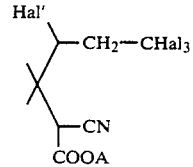

in which Hal' represents a chlorine or bromine atom, in the presence of an acid. The resulting compound is a useful intermediate in the synthesis of certain pyrethroid insecticides.

9 Claims, No Drawings

PROCESS FOR THE PREPARATION OF CYCLOPROPANE COMPOUNDS

BACKGROUND OF THE INVENTION

1. Field of the Invention

This application relates to a process for the preparation of a compound of the formula I

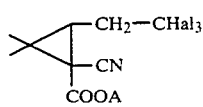

in which each Hal independently represents a chlorine or bromine atom and A represents a hydrogen or metal atom or an alkyl group of 1 to 4 carbon atoms.

2. Description of the Prior Art

There exists a great deal of interest in the preparation of the above cyclopropane compounds, since they are intermediates in the preparation of certain synthetic pyrethroid insecticides. These specific pyrethroids are esters which consist of an acid portion and an alcohol portion, wherein the acid portion is derived from a 3-(2,2-dihalovinyl)-2,2-dimethylcyclopropane carboxylic acid (cf. formula II).

Conventionally, the desired cyclopropane ring is formed by a base-catalyzed cyclization of a suitably substituted compound related to hexanoic acid. In the most general of terms, such reactions can be represented as follows:

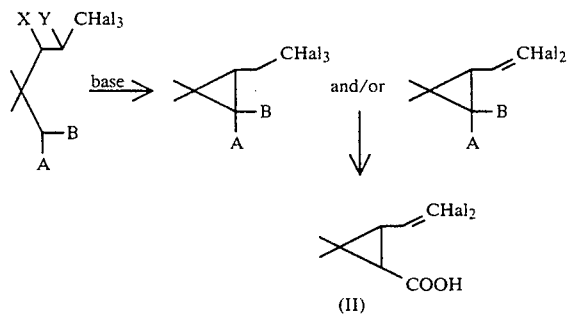

Here Hal is halogen and either X is halogen and Y is hydrogen or X and Y together form an olefinic double bond. In the prior art, A and B can represent a variety of possible groups such that the desired acid (or an ester thereof) can be prepared. Bases employed are both bases in the Bronsted sense, e.g. KOH, and bases in the Lewis sense, e.g. organic amines. Examples of documents in which such reactions are disclosed are German Offenlegungsschrift No. 2606635 and UK specifications Nos. 1561502, 1512419, 1520023 and 1580203.

In general these reactions proceed smoothly and in good yield. However, the cyclization reaction has to be carried out in the presence of a base, which necessitates working up the salts or complexes formed initially in the reaction mixture. In some cases this work-up may be quite complicated due to the formation of salts or complexes, which are difficult to separate. Consequently there is a need for an alternative process which obviates these problems, and which process is generally applicable to the cyclization of cyclopropane compounds too.

Suprisingly it has now been found that the cyclization can be performed in the presence of an acid.

SUMMARY OF THE INVENTION

The invention therefore provides a process for the preparation of a compound of the general formula I

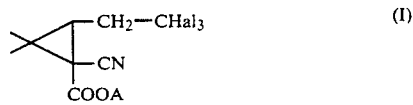

in which each Hal independently represents a chlorine or bromine atom and A represents a hydrogen or metal atom or an alkyl group of 1 to 4 carbon atoms, which comprises cyclizing a compound of the general formula III

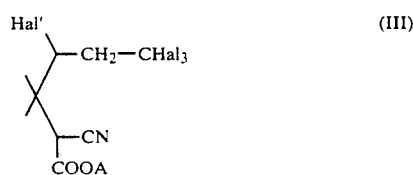

in which Hal' represents a chlorine or bromine atom, in the presence of an acid.

As can be seen from the two formulas I and III, the process comprises a cyclization with a simultaneous expulsion of HHal'. Thus the invention is the more so surprising since HHal', i.e. HCl or HBr, is an acid per se, and so it is not expected to be driven out in an acid environment. Moreover, the reaction proceeds well with carboxylic acids, an alkali metal or silver salts and esters, and thus is generally applicable.

The acid used may be any acid in the Lewis sense, i.e. any electron acceptor of a suitable strength. Very suitable are typical acidic catalysts such as $AlCl_3$, $AlBr_3$, $BF_3$, or $FeCl_3$, of which $AlCl_3$ is preferred.

Alternatively, the Lewis acid may be "H+" or "$H_3O^+$", as provided by acids in the Brønsted sense, i.e. by proton donors. In fact advantageous results are obtained when the acid is a Brønsted acid, either organic, such as p.toluenesulphonic, benzoic, oxalic and acetic acid, or inorganic, such as arsenic, carbonic, hydrochloric, nitrous, nitric, iodic and periodic acid. Particularly good results are obtained by the use of stronger Brønsted acids, i.e. those acids having a $pK_a$ below 5 and preferably below 2.5, when measured in aqueous solutions at 25° C. Examples of stronger acids are trichloracetic acid, trifluoroacetic acid, sulphuric acid and formic acid. The Brønsted acid preferably is sulphuric acid.

Dissolution in water, however, is not a prerequisite; other solvents than water may be used as well, whereas the cyclization reaction may also be carried out in a pure acid, provided it is a liquid; e.g. glacial acetic acid or concentrated formic acid would be suitable. The cyclization is preferably carried out in an organic liquid medium. Such a medium dissolves, or at lease suspends, all components present in the reaction mixture, in particular the hexanoic acid derivative of formula III and the cyclopropane compound of formula I. Both protic and aprotic liquids of various polarities may be used. For example, nitromethane, ethanol, methanol, toluene, tetrachloromethane, tetrahydrofurane, 1,4-dioxane, 1,2-dichloroethane are all very suitable. However, when using aluminum chloride or the like as the acid, the organic liquid medium should preferably be waterfree, to prevent any degradation of the aluminum chloride, etc. Excellent results have been obtained, both with organic and inorganic Brønsted acids and with Lewis acids, if the organic liquid medium is 1,4-dioxane.

The cyclization reaction can be carried out in any manner suitable to induce ring closure and elimination of HHal'. Conveniently this is accomplished by heating the reaction mixture (i.e. the hexanoic acid derivative of formula III, the acid and, optionally, a solvent) to a temperature of suitably between room temperature and the reflux temperature of the reaction mixture. The cyclization is preferably carried out by heating to a temperature in the range of about 20° C. to about 150° C., especially of about 50° C. to about 110° C. The expelled HHal' either dissolves in the liquid reaction mixture (or in a or the polar liquid layer if a multi-phase system is present), or it evolves as a gas. It may be absorbed externally in a suitable medium like dry or wet CaO, if desired.

It has been observed that the conversion and the yield increase with longer reaction times. Conveniently therefore the reaction is carried out for as long a period as practicable, for instance over night. Advantageously the heating is carried out for a period in the range of about 1 to about 20 hours.

The amount of acid is not crucial: as said above, the reaction can be performed in a substantially pure acid, in which case the acid is present in a large molar excess to the starting compound of formula III—on the other hand, a few drops of acid also suffice to catalyze the reaction. It has been observed, however, that if the acid used is a Brønsted acid, the reaction rate improves if more than one mole of acid is used per mole of starting compound of formula III. Preferably, in other words, the Brønsted acid is present in an amount of more than about 1 molar equivalent, especially of about 1-10 equivalents.

As will be appreciated, the acid of general formula II can exist as two geometric isomers, in which the —CH=CHal$_2$ and —CO$_2$H groups are cis or trans to each other. (Each of these geometric isomers, of course, exists as two optical isomers, or enantiomers). Synthetic pyrethroids in which the acid portion is in the cis form are in general more active as insecticides than the corresponding trans compound. One of the problems associated with the cyclization reaction in general is that it usually tends to produce a mixture of the two geometric isomers. Much research has been directed towards the development of a process which produces the desired cis acid in large excess over the trans acid. For instance, European Pat. No. 3683 describes one such process, in which the compound cyclized is an ester, and cyclization occurs in such a way that the halogen-containing group and the ester group are cis to each other. Another process is described in European Pat. No. 64,781 in which a specific type of hexanoic acid derivative as starting material, a specific type of base and a specific type of reaction medium permit the cyclization to occur in such a way that the resulting cyclopropane compound (present formula I) contains a carboxyl group and a halogen containing group trans to each other, which intermediate compound can be converted readily into the desired cis acid or ester.

As an additional advantage of the present invention, the Applicant has now found that when using a specific type of acid and a specific solvent, cyclization can occur to give a cyclopropane compound containing the —COOA group and the —CH$_2$—CHal$_3$ group trans to each other. By then decarboxylating to remove the COOA group, e.g. in the presence of water and the absence of a copper salt, hydrolyzing the CN group, e.g. with base, and dehydrohalogenating, e.g. with base, the desired cis cyclopropane acid can be prepared (cf. formulas I and II).

Accordingly, the invention also provides a process as described hereinabove for the preparation of a compound of the general formula I having a high content of the trans isomer, characterized in that the cyclization is carried out in 1,4-dioxane in the presence of sulphuric acid.

The terms "trans" applied to the compounds of formula I means the isomer (enantiomer pair) in which the —CH$_2$—CHal$_3$ group and the —COOA group are trans to each other, thus:

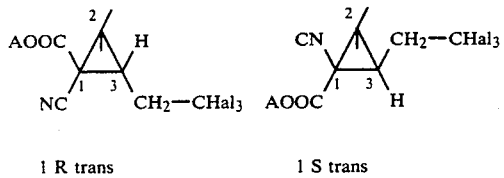

1 R trans      1 S trans and the term "cis" should be construed accordingly. The term "high content" applied to the trans isomer should be understood to mean that the trans isomer is present in an amount of at least 60% of cis and trans compounds combined, i.e. that the trans:cis ratio is at least 60:40. In practice, it is possible by using the process according to the invention under optimum conditions to obtain trans:cis ratios much higher than 60:40.

The starting material III may be prepared by any suitable method, for example by reaction of the compound:

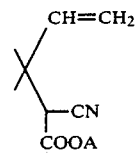

with a carbon tetrahalide CHal$_3$Hal', in the presence of a catalyst, for example an iron salt plus benzoin. If this reaction is carried out in the presence of a suitable solvent system, for example in excess CHal$_3$Hal' optionally together with a suitable co-solvent, the reaction mixture resulting, containing the compound III, may be reacted directly in the process according to the invention without intermediate work-up.

The following Examples illustrate the invention. Analyses were carried out using NMR spectroscopy and/or gas liquid chromatography.

EXAMPLE I

A solution of 0.4 g of ethyl 4-bromo-6,6,6-trichloro-2-cyano-3,3-dimethylhexanoate, 5 ml of 1,4-dioxane and 5 ml of 10% aqueous HCl (100 g/l) was heated under reflux for 4 hours, i.e. at about 100° C. Analysis of the product by NMR showed a conversion of 60% with 100% selectivity to ethyl 2,2-dimethyl-3-(2,2,2-trichloroethyl)-1-cyanocyclopropane carboxylate. The cis:trans ratio was 1:1.

EXAMPLES II–XVII 4,6,6,6-Tetrachloro-2-cyano-3,3-dimethylhexanoic acid was dissolved in equal amounts in different solvents, and different acids were added thereto to induce ring closure to yield 1-cyano-2,2-dimethyl-3-(2,2,2-trichloroethyl)-cyclopropane carboxylic acid (A). The experimental conditions and the results are collected in the Table. Every reaction mixture was heated to its reflux temperature.

TABLE

| Example | acid (molar equivalents) | solvent | reaction time (hours) | yield of A % molar | cis:trans ratio |
| --- | --- | --- | --- | --- | --- |
| II | 0.25 AlCl₃ | 1,2-dichloroethane | 18 | 40 | 50:50 |
| III | 0.50 AlCl₃ | dry 1,4-dioxane | 16 | 50 | 50:50 |
| IV | 0.50 AlCl₃ | dry 1,4-dioxane | 2 | 66 | 40:60 |
| V | 0.25 AlCl₃ | nitromethane | 16 | 60 | 45:55 |
| VI | 1.50 AlCl₃ | dry 1,4-dioxane | 2 | 50 | 40:60 |
| VII | 1.50 AlCl₃ | dry 1,4-dioxane | 5 | 70 | 40:60 |
| VIII | 0.15 H₂SO₄ | ethanol | 1.5 | 70 | 30:70 |
| IX | 1.5 H₂SO₄ | ethanol | 2 | 30 | 20:80 |
| X | 1.5 H₂SO₄ | 1,4-dioxane | 2 | 35 | 10:90 |
| XI | 1.5 H₂SO₄ | 1,4-dioxane | 5 | 35 | 10:90 |
| XII | 0.5-p-toluene-sulphonic acid | 1,4-dioxane | 16 | 20 | 20:80 |
| XIII | 2.0-p-toluene-sulphonic acid | 1,4-dioxane | 16 | 20 | 20:80 |
| XIV | CF₃COOH | CF₃COOH | 4 | 20 | 20:80 |
| XV | CF₃COOH | CF₃COOH | 24 | 40 | 20:80 |
| XVI | HCl gas | 1,4-dioxane | 5 | 90 | 45:55 |
| XVII | HCOOH | HCOOH | 5 | 30 | 20:80 |

What is claimed is:

1. A process for the preparation of a compound of the formula I

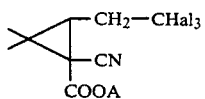

(I)

in which each Hal independently represents a chlorine or bromine atom and A represents a hydrogen, an alkali metal or silver metal atom or an alkyl group of 1 to 4 carbon atoms, which comprises cyclizing a compound of the formula III

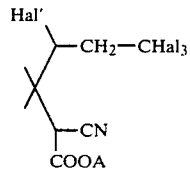

(III)

in which Hal' represents a chlorine or bromine atom, in the presence of a Lewis acid.

2. A process according to claim 1, wherein that the acid is a Bronsted acid.

3. A process according to claim 2, wherein that the Bronsted acid is sulphuric acid.

4. A process according to claim 1 wherein that the cyclization is carried out in an organic liquid medium.

5. A process according to claim 4, wherein that the organic liquid medium is 1,4-dioxane.

6. A process according to claim 1 characterized in that the cyclization is carried out by heating to a temperature in the range of about 20° C. to about 150° C.

7. A process according to claim 6, wherein that the heating is carried out for a period in the range of about 1 to about 20 hours.

8. A process according to claim 2 wherein that the Bronsted acid is present in an amount of more than about 1 molar equivalent.

9. A process according to claim 1 for the preparation of a compound of the formula I having a high content of the trans isomer, characterized in that the cyclization is carried out in 1,4-dioxane in the presence of sulphuric acid.

* * * * *